United States Patent [19]

de Souza et al.

[11] Patent Number: 5,268,471
[45] Date of Patent: Dec. 7, 1993

[54] PROCESS FOR THE PREPARATION OF 6-ACYL, 7-ACYL, AND 6,7-DIACYL ANALOGUES OF FORSKOLIN AND INTERMEDIATES THEREOF

[75] Inventors: Noel J. de Souza; Premanand D. Desai, both of Bombay; Shrikant V. Savanur, Pin; Jürgen Blumbach, Bombay, all of India

[73] Assignee: Hoechst Aktiengesellschaft, Frankfurt am Main, Fed. Rep. of Germany

[21] Appl. No.: 5,163

[22] Filed: Jan. 15, 1993

Related U.S. Application Data

[63] Continuation-in-part of Ser. No. 733,811, Jul. 22, 1991, abandoned.

[30] Foreign Application Priority Data

Jul. 24, 1990 [EP] European Pat. Off. ........ 90114126.7

[51] Int. Cl.$^5$ ................. C07D 405/12; C07D 311/92
[52] U.S. Cl. .................................... 540/596; 544/150; 544/375; 546/196; 548/525; 549/389
[58] Field of Search .................. 549/389; 546/196; 548/525; 544/150, 375

[56] References Cited

FOREIGN PATENT DOCUMENTS 2205564A 12/1988 United Kingdom .

OTHER PUBLICATIONS

*Synthesis* pp. 661 and 665 (1977).

Primary Examiner—C. Warren Ivy
Assistant Examiner—A. Owens
Attorney, Agent, or Firm—Finnegan, Henderson, Farabow, Garrett & Dunner

[57] ABSTRACT

Process for the preparation of 6-acyl-, 7-acyl- or 6,7-diacyl analogues of forskolin of the general formula

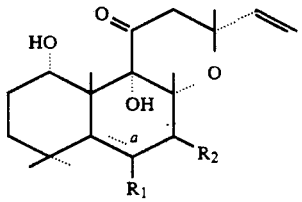

9 Claims, No Drawings

PROCESS FOR THE PREPARATION OF 6-ACYL, 7-ACYL, AND 6,7-DIACYL ANALOGUES OF FORSKOLIN AND INTERMEDIATES THEREOF

This application is a continuation-in-part of application Ser. No. 07/733,811, filed Jul. 22, 1991, now abandoned.

The present invention relates to a novel process for the preparation of 6-acyl, 7-acyl, 6,7-diacyl analogues of forskolin and its derivatives and pharmaceutically acceptable salts thereof, which are useful as medicinal agents. The compounds of the invention are represented by the general formula I,

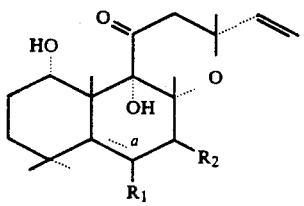
I wherein $R_1$ and $R_2$, which may be equal or different, stand for hydroxyl, acetoxy, a group

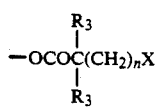

wherein $R_3$ stands for
hydrogen or alkyl,
n stands for the
integer 0 to 10,
X stands for
hydrogen, halogen, alkyl or a group $NR_4R_5$,
wherein
$R_4$ and $R_5$ when they are the same stand for hydrogen or alkyl; when they are not the same $R_4$ stands for hydrogen and $R_5$ stands for alkyl, aryl, aralkyl or substituted alkyl; or $R_4$ and $R_5$ together with the nitrogen to which they are attached form a heterocycle which may contain an additional heteroatom such as N, O, S, or more than one heteroatom and may optionally be substituted at one or more positions by substituents such as halogen, alkyl, hydroxy, alkoxy, carboxyl, nitro, or cyano group;
or a group $-OCONR_6R_7$ wherein $R_6$ and $R_7$ have the same meaning as defined above for $R_4$ and $R_5$, respectively;

'a' stands for an optional additional bond between the carbon atoms C-5 and C-6, with the proviso that when it is present, $R_1$ stands for hydrogen only and $R_2$ has the same meaning as defined above, and pharmaceutically acceptable salts thereof.

The term alkyl stands for a straight or branched chain containing 1-6, preferably 1-4 carbon atoms such as methyl, ethyl, isopropyl, n-butyl, tert. butyl or pentyl, preferably methyl.

The term aryl stands for phenyl which may optionally be substituted at one or more positions by groups such as $C_1$-$C_4$-alkyl, $C_1$-$C_4$-alkoxy, hydroxy, halogen, preferably chlorine or fluorine, cyano, nitro or trifluoromethyl.

The term aralkyl stands for the benzyl group, wherein phenyl has the same above meaning.

The term heterocycle stands for groups such as e.g. piperidino, morpholino, piperazino, pyrrolidino or homopiperadino which may be substituted preferably by $C_1$-$C_4$-alkyl.

Pharmaceutically acceptable salts means inorganic acid addition salts such as e.g. the hydrochloride, hydrobromide, sulphate or phosphate or an organic acid addition salt such as e.g. the salt of formic acid, acetic acid, fumaric acid, maleic acid, citric acid, tartaric acid, lactic acid or methanesulphonic acid.

In the inventive process, compounds of the general formula I are advantageously prepared from 1α,9α-O-isopropylidene derivatives of forskolin and its derivatives represented by the general formula II wherein $R_1$, $R_2$ and "a" have the same meanings as defined above.

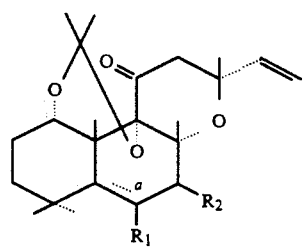
II

Prior Art

Known processes for the preparation of compounds of the formula I include those which comprise acylating the 7-OH group of the compounds of the general formula III, wherein 'a' and $R_1$ have the

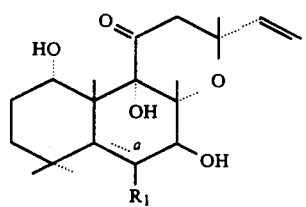
III same meanings as defined earlier, (a) directly, without the use of protecting groups at the 1-OH or 1-OH/9-OH positions, but with tedious methods of (i) separating the resulting 1-acylated isometric products obtained together with compounds of formula I, or (ii) selectively, removing the acyl group at the 1-position (Patent Nos. E.P.A. 0193132, Indian Patent No. 163242 and Ger. Appl. No. P 3535086.5. E.P.A. 0222413, J.P.A. 159638).

(b) by protecting the 1-OH group with a protecting group such as t-butyldimethyl silyl or methoxyethoxymethyl, and removing the protecting group after acyl groups as defined in Formula I have been introduced at the 7-OH and/or 6-OH group, (Patent Nos. E.P. 0193132 and E.P. 0222413, Indian Patent No. 164675 and Ger. Appl. No. P 3623300.5, Indian Patent Appl. No. 266/BOM/87 and Ger. Appl. No. P 3740625.6).

(c) by protecting the 1-OH group together with the 9-OH group with groups such as carbonyl (C=O), thiocarbonyl (C=S), =CNNRR'7, and removing the 1,9-protecting group after acyl groups as defined have been introduced at the 7-OH and/or 6-OH group. (Patent No. E.P. 0193132).

All of the processes of the prior art have disadvantages. Those processes in which direct acylation of the 7-OH group is carried out are limited by the low selectivity of acylation at the 7-OH group in presence of the free 1-OH group.

Those processes which use a step of removing the acyl group at the 1-acyloxy position from a 1,6-diacyloxy-, 1,7-diacyloxy or 1,6,7-triacyloxy derivative are limited by the low selectivity of deacylation at the 1-position in the presence of 6-acyloxy-, 7-acyloxy-, or 6,7-diacyloxy- groups.

Those processes which use protective groups at the 1-OH or 1-OH/9-OH positions are limited by the nature of the reagents used for protection/deprotection which are expensive, not readily available commercially or subjected to severe process conditions resulting in lowered yields of the desired compounds I.

Present Invention

The present invention arises from in-depth studies and findings that highly pure 6-acyl-, 7-acyl- or 6,7-diacyl analogues of forskolin and its derivatives of the formula I can surprisingly be readily and economically prepared by first using 1,9-isopropylidene protected intermediates to prepare the corresponding 6-acyl-, 7-acyl-, or 6,7-diacyl analogues through conventional acylation and/or acyl migration methodologies, and then removing the 1,9-O-isopropylidene group, by treatment with an appropriate reagent as specified below. Scheme I illustrates the preparation of the said novel 1,9-O-isopropylidene derivatives of appropriate 6-acyl-, 7-acyl- and 6,7-diacyl forskolin analogues of the formula II (Scheme I, formulae 1-5), of the invention.

A further crucial and integral part of the invention is the removal of the 1,9-O-isopropylidene protecting group. Such a removal is well-documented for other compounds in the literature and is generally done with the use of acidic reagents such as e.g. acetic acid, hydrochloric acid, perchloric acid or ion exchange resins. These reported methods, however, when used as described for the compounds of the invention which bear acid-labile groups at the 6- and/or 7-position generally result in product mixtures containing compounds in which the 6- and/or 7-acyl groups have also cleaved.

It is now a surprising finding that the 1,9-O-isopropylidene compounds of this invention may be preferentially deprotected at the 1-, 9-positions without significant effect at the 6- and/or 7-acyl groups by treatment in solution at a pH value of about 1.0–3.5 preferably at pH 1.0–1.3, at temperatures ranging from about 0° C. to 80° C., preferably at 25°–60° C. for a period up to about 72 hours, preferably for less than 1 hour up to 24

Scheme I

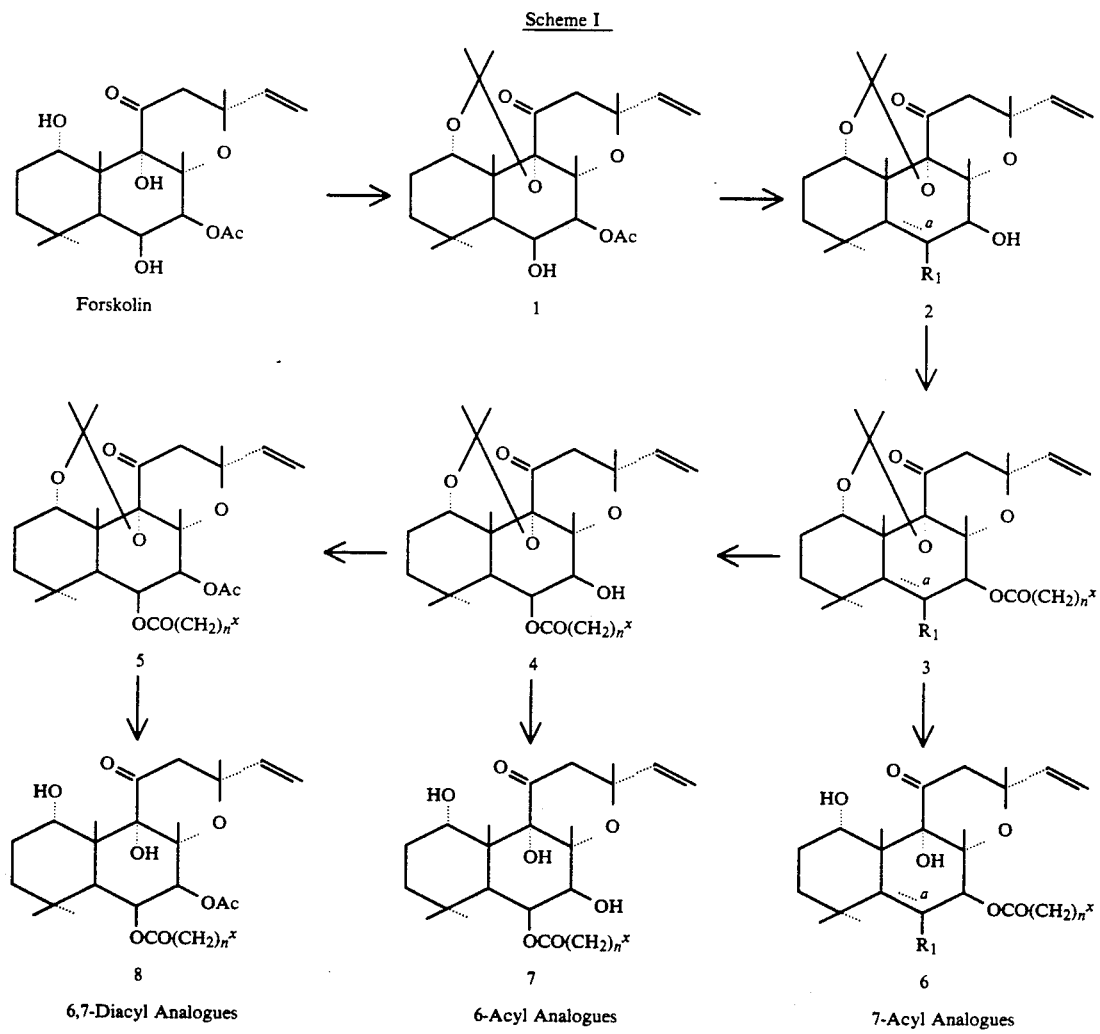

6,7-Diacyl Analogues     6-Acyl Analogues     7-Acyl Analogues hours. Other preferred temperature ranges are from 30° C. to 40° C. and from 15° C. to 20° C. Scheme I also illustrates the deprotected compounds I of the invention (Scheme I, formulae 6–8).

The compounds of Formula II of the invention which are specifically claimed are listed in Tables I–III.

TABLE I

7β-Substituted-8,13-epoxy-6β-hydroxy-1α,9α-O-isopropylidene-labd-14-en-11-ones

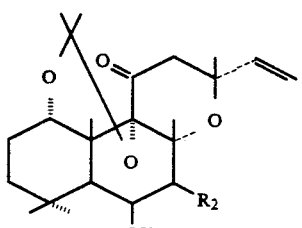

| Compound | $R_2$ | M.P. (°C.) |
|---|---|---|
| 1 | $OCOCH_3$ | 228 |
| 2 | OH | 116–119 |
| 3 | $OCOCH_2Cl$ | 167–168 |
| 4 | $OCO(CH_2)_2Cl$ | 203–204 |
| 5 | $OCO(CH_2)_3Cl$ | 135–138 |
| 6 | $OCOCH_2N\!\!\left\langle\begin{array}{c}\\\end{array}\right\rangle$ (piperidine) | 70–72 |
| 7 | $OCO(CH_2)_2N\!\!\left\langle\begin{array}{c}\\\end{array}\right\rangle$ (piperidine) | 114–116 |
| 8 | $OCO(CH_2)_2N(CH_3)_2$ | 194–195 |
| 9 | $OCO(CH_2)_3N\!\!\left\langle\begin{array}{c}\\O\end{array}\right\rangle$ (morpholine) | 172–174 |

TABLE II

7β-Substituted-8,13-epoxy-1α,9α-O-isopropylidene-labd-5,14-dien-11-ones

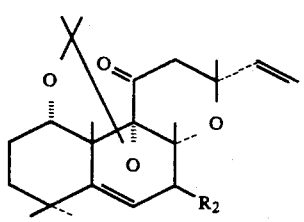

| Compound | $R_2$ | M.P. (°C.) |
|---|---|---|
| 10 | OH | Oil |
| 11 | $OCOCH_3$ | Oil |
| 12 | $OCON\!\!\left\langle\begin{array}{c}\\=N\end{array}\right\rangle$ (imidazole) | 160–161 |
| 13 | $OCONHCH_3$ | 182–183 |

TABLE III

6β,7β-Disubstituted-8,13-epoxy-1α,9α-O-isopropylidene-labd-14-en-11-ones

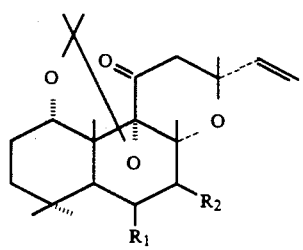

| Compound No. | $R_1$ | $R_2$ | M.P. °C. |
|---|---|---|---|
| 14 | $OCOCH_2N\!\!\left\langle\begin{array}{c}\\\end{array}\right\rangle$ (piperidine) | OH | 213–215 |
| 15 | $OCO(CH_2)_2N(CH_3)_2$ | OH | Oil |
| 16 | $OCO(CH_2)_2N\!\!\left\langle\begin{array}{c}\\\end{array}\right\rangle$ (piperidine) | OH | Oil |
| 17 | $OCOCH_2N\!\!\left\langle\begin{array}{c}\\\end{array}\right\rangle$ (piperidine) | $OCOCH_3$ | 143–144 |
| 18 | $OCO(CH_2)_2N\!\!\left\langle\begin{array}{c}\\\end{array}\right\rangle$ (piperidine) | $OCOCH_3$ | Oil |
| 19 | $OCO(CH_2)_2N(CH_3)_2$ | $OCOCH_3$ | Oil |

The compounds of formula I of the invention which are specifically claimed are as shown in Tables IV–V.

TABLE IV

6β,7β-Disubstituted-1α,9α-dihydroxy-8,13-epoxy-labd-14-en-11-ones

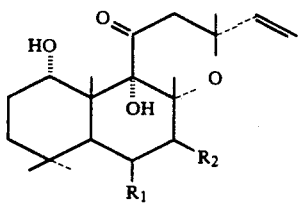

| Compound No. | $R_1$ | $R_2$ | Salt | M.P. °C. |
|---|---|---|---|---|
| 20 | $OCOCH_2N\!\!\left\langle\begin{array}{c}\\\end{array}\right\rangle$ (piperidine) | OH | HCl | 197–98 |
| 21 | $OCOCH_2N\!\!\left\langle\begin{array}{c}\\\end{array}\right\rangle$ (piperidine) | $OCOCH_3$ | — | 222–223 |

TABLE IV-continued

6β,7β-Disubstituted-1α,9α-dihydroxy-8,13-epoxy-labd-14-en-11-ones

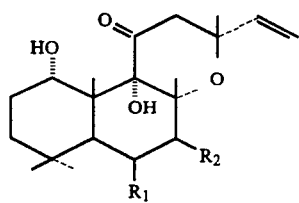

| Compound No. | R₁ | R₂ | Salt | M.P. °C. |
|---|---|---|---|---|
| 22 | OCO(CH₂)₂N(piperidine) | OCOCH₃ | HCl, 0.5H₂O | 237–239 |
| 23 | OCO(CH₂)₂N(CH₃)₂ | OH | — | 162–163 |
| 24 | OCO(CH₂)₂N(CH₃)₂ | OCOCH₃ | — | 183–184 |
| 25 | OCO(CH₂)₂N(CH₃)₂ | OCOCH₃ | HCl | 265–269 |

TABLE V

7β-Substituted-1α,9α-dihydroxy-5,13-epoxy-labd-5,14-dien-11-ones

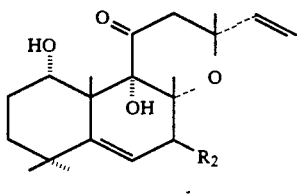

| Compound | R₂ | M.P. (°C.) |
|---|---|---|
| 26 | OCONHCH₃ | 110–112 |

The present invention has thus been accomplished on the basis of these findings.

Examples of acyloxy group in the general formulae I and II include acyl such as acetyloxy, haloacyl such as chloroacetyloxy, chloropropionyloxy, chlorobutyryloxy, aminoacyl such as piperidinoacetyloxy, 2-piperidinopropionyloxy, 2-N-methylpiperazinopropionyloxy, 2-dimethylaminopropionyloxy, 3-morpholinobutyryloxy, imidazolylcarbonyloxy, methylaminocarbonyloxy.

Examples of compounds of the general formula II are 8,13-Epoxy-6β,7β-dihydroxy-1α,9α-O-isopropylidene-labd-14-en-11-one (compound No. 2).

7β-chloroacetyloxy-8,13-epoxy-6β-hydroxy-1α,9α-O-isopropylidene-labd-14-en-11-one, (compound No. 3).

7β-(3-chloropropionyloxy)-8,13-epoxy-6β-hydroxy-1α,9α-O-isopro-pylidene-labd-14-en-11-one, (Compound No. 4).

7β-(4-chlorobutyryloxy)-8,13-epoxy-6β-hydroxy-1α,-9α-O-isopropylidene-14-en-11-one, (Compound No. 5).

7β-piperidinoacetyloxy-8,13-epoxy-6β-hydroxy-1α,9α-O-isopropylidene-labd-14-en-11-one, (Compound No. 6).

7β-(3-piperidinopropionyloxy)-8-13-epoxy-6β-hydroxy-1α,9α-O-isopropylidene-labd-14-en-11-one, (Compound No. 7).

7β-(3-dimethylaminopropionyloxy)-8,13-epoxy-6β-hydroxy-1α,9α-O-isopropylidene-labd-14-en-11-one, (Compound No. 8).

7β-(4-morpholinobutyryloxy)-8,13-epoxy-6β-hydroxy-1α,9α-O-isopropylidene-labd-14-en-11-one (Compound No. 9).

6β-(piperidinoacetyloxy)-8,13-epoxy-7β-hydroxy-1α,-9α-O-isopropylidene-labd-14-en-11-one, (Compound No. 14).

6β-(3-piperidinopropionyloxy)-8,13-epoxy-7β-hydroxy-1α,9α-O-isopropylidene-labd-14-en-11-one, (Compound No. 16).

6β-(3-dimethylaminopropionyloxy)-8,13-epoxy-7β-hydroxy-1α,9α-O-Isopropylidene-labd-14-en-11-one, (Compound No. 15).

7β-Acetoxy-6β-piperidinoacetyloxy-8,13-epoxy-1α,9α-O-isopropylidene-labd-14-en-11-one, (Compound No. 17).

7β-Acetoxy-6β-(3-dimethylaminopropionyloxy)-8,13-epoxy-1α,9α-O-isopropylidene-labd-14-en-11-one, (Compound No. 19).

7β-Acetoxy-6β-(3-piperidinopropionyloxy)-8,13-epoxy-1α,9α-O-isopropylidene-labd-14-en-11-one, (Compound No. 18).

8,13-Epoxy-7α-hydroxy-1α,9α-O-isopropylidene-labd-5,14-dien-11-one (Compound No. 10).

7β-Acetoxy-8,13-epoxy-1α,9α-O-isopropylidene-labd-5,14-dien-1-one (Compound No. 11).

7β-imidazolylcarbonyloxy-8,13-epoxy-1α,9α-O-isopropylidene-labd-5,14-dien-11-one (Compound No. 12).

7α-(N-methylaminocarbonyloxy)-8,13-epoxy-1α,9α-O-isopropylidene-labd-5,14-dien-11-one, (Compound No. 13).

Examples of compounds of the formula I include:
6β-piperidinoacetyloxy-1α,7β,9α-trihydroxy-8,13-epoxy-labd-14-en-11-one, (Compound No. 20).

6β-(3-dimethylaminopropionyloxy)-1α,7β,9α-trihydroxy-8,13-epoxy-labd-14-en-11-one, (Compound No. 23).

7β-acetoxy-6β-(piperidinoacetyloxy)-1α,9α-dihydroxy-8,13-epoxy-labd-14-en-11-one, (Compound No. 21).

7β-acetoxy-6β-(3-dimethylaminopropionyloxy)-1α,9α-dihydroxy-8,13-epoxy-labd-14-en-11-one (Compound No. 24).

7β-acetoxy-6β-(3-dimethylaminopropionyloxy)-1α,9α-dihydroxy-8,13-epoxy-labd-14-en-11-one hydrochloride (Compound No. 25).

7β-acetoxy-6β-(3-piperidinopropionyloxy)-1α,9α-dihydroxy-labd-5,14-dien-11-one hydrochloride hemihydrate (Compound No. 22).

7β-(N-methylaminocarbonyloxy)-8,13-epoxy-1α,9α-dihydroxy-labd-5,14-dien-11-one, (Compound No. 26).

The 1,9-O-isopropylidene protecting group is introduced in a manner known per se (e.g. Synthesis 1989, pp. 711–713).

The 5-en double bond can also be obtained by conventional methods known from literature.

Examples of the acylating agent are 1,1'-carbonyldiimidazole, acetic acid, propionic acid, butyric acid and reactive derivatives thereof such as e.g. acid halides or acid anhydrides.

The acylation of the compounds of formula II in which R₂ is OH is carried out by using about 2 to 3 moles of an acylating agent per mole of the compound in the presence of a base such as pyridine for a period of about 0.5 to 48 hours, preferably 2 to 24 hours optionally using solvents such as benzene, chloroform, ether, and under cooling with ice, or heating at a higher temperature up to about the boiling point of the solvent used.

When migration of the 7-acyl group to the 6-OH group has to be done, the appropriate compound is treated by one of two methods as follows:
(a) treatment of the 7-aminoacyloxy compound with an inorganic base such as e.g. NaOH, KOH, $Na_2CO_3$, NaH in organic solvents such as e.g. methanol, acetone, acetonitrile, dioxane, dimethylsulfoxide, N,N-dimethylformamide of tetrahydrofuran or a mixture of water with each of the solvents, preferably a mixture of acetonitrile and water. The reaction is conducted for a period from about 10 minutes to 24 hours preferably for a period from 30 minutes to 1 hour and preferably at room temperature.
(b) heating the 7-aminoacyloxy compound to the temperature to form a melt under stirring and nitrogen atmosphere for a period of about 15 minutes to one hour, optionally using anhydrous solvents such as N-N-dimethylformamide, dimethylsulfoxide, diglycone, nitrobenzene or chlorobenzene.

The preparation of 7-carbamoyloxy compounds such as compound 13 in Table II, is carried out by treating a 7-imidazolylcarbonyloxy derivative (Table II, Compound 12) with an appropriate amine using organic solvents such as ethylacetate, chloroform, toluene at temperatures from about 0° to boiling point of the solvent, preferably at room temperature for a period of about 1 hour to 48 hours.

The removal of the 1,9-O-isopropylidene group in compounds of formula II is carried out by treating the compound in aqueous solution, the pH of which is adjusted to about 1.0–3.5, preferably 1.0–1.3 with the use of acidic reagents such as e.g. aqueous hydrochloric acid, acetic acid or orthophosphoric acid, alone or as mixtures, or with the use of buffer reagents, or with the use of ion exchangers, optionally in the presence of solvents such as e.g. ethanol or tetrahydrofuran, at temperatures from about 0° C. to 80° C. preferably at 25° to 60° C., for a period up to about 72 hours, preferably <1 to 24 hours. The product may be obtained by crystallisation from the reaction mixture or by neutralising the reaction mixture, extracting with organic solvent, washing the organic layer with water, drying over dehydrating agents such as sodium sulphate, filtering and concentrating under vacuum. The residue obtained is purified by crystallisation.

The compounds of the invention are, if desired, converted into pharmaceutically acceptable salts such as a hydrochloride by conventional procedures.

Improvements in yields obtained of some of the compounds of the invention, such as 7β-Acetoxy-6β-(3-N-dimethylaminopropionyloxy)-1α,9α-dihydroxy-8,13-epoxy-labd-14-en-11-one and 1α,9α-Dihydroxy-7β-(N-methylamino carbonyloxy)-8,13-epoxy-labd-5,14-dien-11-one, when prepared by the process of the invention in comparison to those reported in the prior art are listed in Table VI.

TABLE VI

| Compound | | |
|---|---|---|
| 7β-Acetoxy-6β-(3-N-dimethylaminopropionyloxy-1α,9α-dihydroxy-8,13-epoxy-labd-14-en-11-one | J.P.A. 159638 | 54% (based on 6β-(3-N-dimethylaminopropionyloxy-8,13-epoxy-1α,9α,7β-tri-hydroxy-labd-14-en-11-one) |
| | Present Invention Example 9 addenda | 79% (based on 7β-hydroxy-6β-(3-N-dimethylamino-propionyloxy)-8,13-epoxy 1,9-0-isopropylidene-labd-14-en-11-one) |
| 1α,9α-Dihydroxy-7β-(N-methylaminocarbonyloxy)-8,13-epoxy-labd-5,14-dien-11-one | Indian Pat. Appl. No. 266/BOM/87 (using 1-t-butyl-dimethylsilyl protection group) | 45% (based on forskolin) |
| | Present Invention Example 9 | 61% (based on forskolin) |

The following examples illustrate the invention but do not limit the scope of the invention.

Example 1

6β,7β-Dihydroxy-8,13-epoxy-1α,9α-O-isopropylidene-labd-14-en-11-one

Forskolin (51.25 g, 0.125 mole) was dissolved in anhydrous acetone (46 ml) and ether (75 ml). An ethereal solution of aluminum chloride (20 g, 0.15 mole); dissolved in 75 ml anhydrous ether) was added dropwise with stirring at room temperature. The reaction mixture was stirred at the same temperature for 2-3 hours. After completion of the reaction, the mixture was diluted first with ethylacetate (250 ml) and then with cold water (50 ml). The organic layer was separated and evaporated to dryness. The residue was dissolved in methanol (500 ml), 4% aqueous sodium hydroxide (125 ml) was added and the mixture stirred at room temperature for 18 hours. On removing methanol in vacuo the desired compound (41 g) was obtained as a precipitate and was filtered. The filtrate was extracted with ethylacetate to give a further 5 g of the required compound, m.p. 116°–118° C. Yield 90.2%.

Example 2

7β-Hydroxy-8,13-epoxy-1α,9α-O-isopropylidene-labd-5,14-dien-11-one

To a stirred solution of 7β-acetoxy-8,13-epoxy-6β-hydroxy-1α,9α-O-isopropylidene-labd-14-en-11-one (90 g; 0.2 mole) in dichloromethane (200 ml) and pyridine (38.5 ml; 0.48 mole), solution of thionyl chloride (17.5 ml; 0.24 mole) in dichloromethane (100 ml) was added drop-wise at room temperature. After the addition of thionyl chloride solution, the reaction mixture temperature was raised to 40° C. and maintained with stirring (at that temperature) for 3 hours. The reaction mixture was cooled to room temperature and washed with 5% cold aqueous hydrochloric acid solution, followed by 5% sodium bicarbonate solution quickly, and brine, and dried (Na₂SO₄). The solvent was removed under reduced pressure and the oily product obtained was dissolved in methanol (660 ml) and to it was added sodium hydroxide solution (16 g dissolved in 160 ml water) slowly at room temperature. After the addition of sodium hydroxide solution, the reaction mixture was heated to 40° C. and stirred for 2 hours. The reaction mixture was concentrated under vacuo to one-fourth of its volume in order to remove methanol. The separated oily product was extracted with ethyl acetate, and the extract was washed with brine, and dried (Na₂SO₄). The solvent was removed under reduced pressure and the product was purified by passing through a small silica-gel column using 10% ethyl acetate-petroleum ether (40-60) as eluant. Yield 75.5 g (97.8%).

Example 3

7β-chloroacetoxy-8,13-epoxy-6β-hydroxy-1α,9α-O-isopropylidene-labd-14-en-11-one

To a stirred solution of 6,7β-Dihydroxy-8,13-epoxy-1α,9α-O-isopropylidene-labd-14-en-11-one (2.0 g 0.005M) in dichloro-methane (20 ml) and pyridine 0.8 ml (0.01M) solution of chloroacetylchloride (0.42 ml) in dichloromethane (5 ml) dropwise with cooling (at 0°-5° C.). After the addition stirring was continued for 3 hours at room temperature. The reaction mixture was then diluted with ethylacetate and organic layer washed with water, 5% aqueous hydrochloric acid, water and dried over anhydrous Na₂SO₄. After filtration and concentration the solid residue obtained was crystallised to obtained 2.2 gm of the desired compound, yield 92%. m.p. 167°-168° C.

Following the procedure described using chloropropionyl chloride and chlorobutyrylchloride in place of chloroacetylchloride corresponding compounds Nos. 4 and 5 reported in Table I was obtained.

Example 4

1α,9α-O-Isopropylidene-7β-imidazolylcarbonyloxy-8,13-epoxy-labd-5,14-dien-11-one 1α,9α-O-Isopropylidene-7β-hydroxy-8,13-epoxy-labd-5,14-dien-11-one (75 g; 0.19 mole) and diimidazolylcarbonyl (42.12 g; 0.26 mole) in dry ethyl acetate (400 ml) were stirred at 50° C. for 15 hours. After completion of the reaction, the mixture was washed with 5% cold hydrochloric acid, and brine, and dried (Na₂SO₄). The solvent was removed under reduced pressure and the residue was crystallized from 10% ethyl acetate/petroleum ether. Yield 92.2 g (98.8%) mp 160°-161° C.

Example 5

1α,9α-O-Isopropylidene-7β-(N-methylaminocarbonyloxy)-8,13-epoxy-labd-5,14-dien-11-one To a solution of 1α,9α-O-isopropylidene-7β-imidazolylcarbonyloxy-8,13-epoxy-labd-5,14-dien-11-one (obtained from step IV) and methylamine hydrochloride (1 g) in dry ethyl acetate (450 ml), a toluene solution of methylamine (25% solution, 140 ml) was added in 10 ml portions after every 20 mins over a period of 4.5 h and stirred at room temperature for 48 hrs. After completion of the reaction it was diluted with ethyl acetate (300 ml), washed with 5% cold aqueous hydrochloric acid solution, and brine, and dried (Na₂SO₄). The solvent was removed under reduced pressure and the residue was crystallised from 5% ethyl acetate/petroleum ether. Yield 80 g, (93.56%). mp 182°-183° C.

Example 6

7β-[3-(Piperidinopropionyl)oxy]-8,13-epoxy-6β-hydroxy-1α,9α-O-isopropylidene-labd-14-en-11-one A solution of piperidine (0.9 ml) in chloroform (7 ml) was added to a solution of 7β-[3-(chloropropionyl)oxy]-8,13-epoxy-6β-hydroxy-1α,9α-O-isopropylidene-labd-14-en-11-one (2.0 gm) in anhydrous chloroform (15 ml) and stirred for one hour at room temperature. The reaction mixture was then heated to 60°-65° C. and stirred for an additional 18 hours. Reaction mixture was then washed with brine and organic layer separated, dried and filtered to remove the drying agent. Filtrate concentrated to obtain solid residue, which was purified by column chromatography/crystallisation piperidino to give 7β-[3-piperidinopropionyloxy]-8,13-epoxy-6β-hydroxy-1α,9α-O-isopropylidene-labd-14-en-11-one 1.5 g (69% yield), m.p. 114°-116° C.

Following the procedure described above using dimethylamine and morpholine in place of piperidine with the appropriate 7-chloroacyl-labdane derivative and heating the reaction mixture, compounds No. 6 (72% yield), 8 (90.5% yield) and 9 (74% yield) reported in Table I were obtained.

Example 7

6β-[3-(Piperidinopropionyl)oxy]-8,13-epoxy-7β-hydroxy-1α,9α-O-isopropylidene-labd-14-en-11-one 7β-[3-Piperidinopropionyloxy]-8,13-epoxy-1α,9α-O-isopropylidene-labd-14-en-11-one (1.0 g) was heated at 130°-140° C. for (2 hours) under nitrogen atmosphere and with stirring. After cooling to room temperature, the residue was dissolved in methylene chloride (10 ml), the solution is treated with piperidine (0.1 ml) at room temperature with stirring for 3 hrs. The reaction mixture was evaporated to dryness, the residue was purified by column chromatography to recover 0.5 g of starting material and 0.5 g of product. The recovered starting material was subjected to the same process to obtain an additional 0.2 gm of the desired product. Yield (0.7 g) 70%.

Following the similar procedure described above, compounds No. 14 (50% yield) and 15 (76% yield) of Table III were also obtained.

Example 8

7β-Acetoxy-6β-[3-(piperidinopropionyl)oxy]-8,13-epoxy-1α,9α-O-isopropylidene-labd-14-en-11-one hydrochloride A mixture of 6β-[3-piperidinopropionyloxy]-8,13-epoxy-7β-hydroxy-1α,9α-O-isopropylidene-labd-14-en-11-one (1.0 g), dry pyridine (3.8 ml), 4-dimethylaminopyridine (2 mg) and acetic anhydride (0.6 ml) was stirred at room temperature for 3 hours. Removed pyridine under high vacuum dissolved in ethylacetate. The organic layer was washed with water, dried (anhydrous Na₂SO₄), and filtered, and the filtrate concentrated to give an oily product, which was dissolved in ether and treated with ethereal HCl to obtain the desired compound, yield 90%. m.p.136°-137° C., (Acetone-petroleum ether 60°-80° C.).

Following the procedure described above using appropriate labdane derivative, compounds No. 17 and 19 in Table III were prepared in 70% and 90% yield respectively.

Example 9

1α,9α-Dihydroxy-7β-(N-methylaminocarbonyloxy)-8,13-epoxy-labd-5,14-dien-11-one

1α,9α-O-Isopropylidene-7β-(N-methylaminocarbonyloxy)-8,13-epoxy-labd-5,14-dien-11-one (79.3 g; 0.18 mole), methanol (500 ml), acetic acid (58 ml), and 2N hydrochloric acid (50 ml) were stirred at 65° C. for 48 hours. The reaction mixture was concentrated under vacuo to one fourth of its volume to remove methanol. The oily product solidified on standing or on cooling. The solid was filtered and washed with 10% aqueous methanol solution, the filtrate was extracted with ethyl acetate and the extract evaporated to dryness. The combined product of the solid obtained on filtration and the residue from the filtrate extract was dried under high vacuo at 60° C., and purified by crystallisation using chloroform-petroleum ether (1:1.2). Yield 61 g, (84.8%), mp 110°–112° C.

Following the procedure similar to the one described above with compounds Nos. 14, 15, 17, 18, 19 wherein aqueous solutions of the corresponding hydrochlorides salts adjusted to pH 1.0–1.1 with dilute hydrochloric acid and stirring the mixture at 30°–40° C. for a period of 3–5 hours the corresponding 1,9-dihydroxy compounds, Nos. 20, 23, 21, 22, 24 respectively in yields of 50, 88, 62, 60, 88% respectively, reported in Table IV, were obtained by similar methods as described above or by lyophilising the reaction mixture and crystallising the residue.

Example 10

7β-Acetoxy-1,9-dihydroxy-6β-(3-piperidinopropionyloxy)-8,13-epoxy-labd-14-en-11-one hydrochloride hemihydrate.

A suspension of 7β-acetoxy-6β-(3-piperidinopropionyloxy)-8,13-epoxy-1,9-O-isopropylidene-14-en-11-one (8 g, 0.013M) was stirred with 2N hydrochloric acid (100 ml) at 15°–20° C. After 4 hours the reaction mixture was chilled to 0°–5° C. and basified to pH 9. The reaction mixture was extracted with ethyl acetate, and the organic layer washed with water, brine and dried over anhydrous sodium sulphate. The organic layer was evaporated to dryness to give a residue (7 g). The residue was purified using a silica gel column and eluting with ethyl acetate-petroleum ether (1:1) as an eluent to obtain 7β-acetoxy-1,9-dihydroxy-6β-(3-piperidinopropionyloxy)-8,13-epoxy-14-en-11-one. It was dissolved in dry ether and ethereal hydrogen chloride was added to it. The hydrochloride salt so obtained was crystallized from dichloromethane and petroleum ether (60°–80° C.), yield 4.75 g (60%), m.p. 237°–39° C.

Example 11

7β-Acetoxy-1,9-dihydroxy-6β-[3-(N-dimethylaminopropionyl)oxy]-8,13-epoxy-labd-14-en-11-one hydrochloride A suspension of 7β-acetoxy-6β-[3-(N-dimethylaminopropionyl)oxy]-8,13-epoxy-1,9-O-isopropylidene-labd-14-en-11-one (2.20 g, 4.0 mmole) was stirred with 2N hydrochloric acid (40 ml) at 15°–20° C. After half an hour a clear solution was obtained, which on further stirring for 2.5 hours and chilling to 0° C. provided the desired product in a crystalline form. It was filtered and dried to yield 1.98 g. Yield: 91%, m.p. 265°–267° C.

Following the procedure similar to the one described above with compound Nos. 14, 15, 17, and 19, wherein aqueous solutions of the corresponding hydrochlorides salts were adjusted to pH 1.0–1.1 with dilute hydrochloric acid and stirring the mixture at 15°–20° C. for a period of 3–5 hours, the corresponding 1,9-dihydroxy compounds, Nos. 20, 23, 21, and 24, reported in Table IV, were obtained in yields of 50, 88, 62, and 88%, respectively.

TABLE VII
PMR DATA FOR THE ABOVE WORKING EXAMPLES

Working Examples

Example 1 (Compound No. 2)
PMR(CDCl$_3$): δ=6.00(d of d, J$_{cis}$=10.8Hz, J$_{trans}$=17Hz, vinylic-H), 5.1(d of d, J$_{trans}$=17Hz, J$_{gem}$=2Hz vinylic-H), 4.94(d of d, J$_{cis}$=10.8Hz, J$_{gem}$=2Hz, vinylic-H), 4.44(bt, 6-CH), 4.24(bs, 1 β-CH), 3.96(d, J$_{6,7}$=4Hz, 7-CH), 2.98 (d, J$_{gem}$=18Hz, 12-CH), 2.62 (d, J$_{gem}$=18Hz, 12-CH), 2.1(d, J$_{5,6}$=2Hz, 5 CH)1.6, 1.44, 1.4, 1.08(s, 5×CH$_3$),

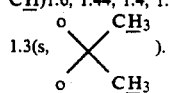

Example 2 (Compound No. 10)
PMR(CDCl$_3$): δ=5.96(d of d, J$_{cis}$=10.8Hz, J$_{trans}$=17Hz, vinylic-H), 5.5(d J$_{6,7}$=2.5 Hz, 7-CH), 5.25(d, J$_{6,7}$=2.5Hz, 6-CH), 5.04(d of d, J$_{trans}$=17Hz, J$_{gem}$=2Hz, vinylic-H), 4.8(d of d, J$_{cis}$=10.8Hz, J$_{gem}$=2Hz, vinylic-H), 4.3 (bt, 1β-CH), 3.16(d, J=18Hz, 12-CH), 2.42(d, J=18Hz, 12-CH), 1.4, 1.36, 1.32, 1.2(s, 5×CH$_3$),

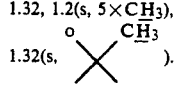

Example 3 (Compound No. 3)
PMR(CDCl$_3$): δ=5.9(d of d, J$_{cis}$=10.8Hz, J$_{trans}$=18Hz, vinylic-H), 5.34(d of d, J$_{6,7}$=4Hz, 7-CH), 5.16(d of d. J$_{trans}$=17Hz, J$_{gem}$=2Hz, vinylic-H), 4.9(d of d, J$_{cis}$=10.8Hz, J$_{gem}$=2Hz, vinylic-H), 4.46 (bt, 6-CH), 4.24(bs, 1β-CH), 4.12(s, 7-O—CO—CH$_2$Cl), 2.98 (d, J$_{gem}$=18Hz, 12-CH), 2.62 (d, J$_{gem}$=18Hz, 12-CH), 2.2(d, J$_{5,6}$=2Hz, 5-CH), 1.68, 1.56, 1.41, 1.3, 1.04(s, 5×CH$_3$),

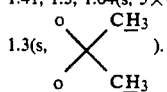

Example 4 (Compound No. 12)
PMR(CDCl$_3$): δ=8.08(s, 2'H) 7.4(s, 5'H), 7.0 (s, 4'H), 6.04(d, J$_{6,7}$=2.5Hz, 7-CH), 5.86(d of d, J$_{trans}$=17Hz, J$_{cis}$=10.8Hz, vinylic H), 5.44(d, J$_{6,7}$=2Hz, 6-CH), 5.16(d of d, J$_{trans}$=17Hz, J$_{gem}$=2Hz, vinylic-H), 4.9(d of d, J$_{cis}$=10.8Hz, J$_{gem}$=2Hz, vinylic-H), 4.28(bt, β1-CH), 3.2(d, J$_{gem}$=18Hz, 12-CH), 2.36(d, J$_{gem}$=18Hz, 12-CH), 1.64, 1.48, 1.46, 1.28, 1.2, 1.16(s, 5×CH$_3$),

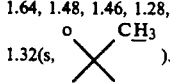

Example 5 (Compound No. 13)
PMR(CDCl$_3$): δ=5.88(d of d, J$_{cis}$=10.8Hz, J$_{trans}$=17Hz, vinylic-H), 5.75(d of d, J$_{6,7}$=2.5Hz, 7-CH), 5.42(d, J$_{6,7}$=2.5Hz, 6-CH), 5.22(d of d, J$_{trans}$=17Hz, J$_{gem}$=2Hz, vinylic-H), 4.92(d of d, J$_{cis}$=10.8Hz, J$_{gem}$=2Hz, vinylic-H), 4.70(bs, NH),

TABLE VII-continued
PMR DATA FOR THE ABOVE WORKING EXAMPLES
Working Examples 4.26(bs, 1β-C$\underline{H}$), 3.2(d, $J_{gem}$=18Hz, 12-C$\underline{H}$), 2.8(d, $J_{NH,CH_3}$=5.4Hz, N-C$\underline{H}_3$), 2.36(d, $J_{gem}$=18Hz, 12-C$\underline{H}$), 1.44, 1.36, 1.28, 1.2(s, 5×C$\underline{H}_3$),

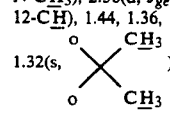

Example 6 (Compound No. 7)
PMR(CDCl$_3$): δ=5.98(d of d, $J_{cis}$=10.8Hz, $J_{trans}$=17Hz, vinylic-$\underline{H}$), 5.14(d of d, $J_{trans}$=17Hz, $J_{gem}$=2Hz, vinylic-$\underline{H}$), 4.97 (d, $J_{6,7}$=4Hz, 7-C$\underline{H}$), 4.9(d of d, $J_{cis}$=10.8Hz, $J_{gem}$=2Hz, vinylic-$\underline{H}$), 4.64(bt, 6-C$\underline{H}$), 4.26(bt, 1β-C$\underline{H}$), 3.6 (d, $J_{gem}$=18Hz, 12-C$\underline{H}$), 2.62(d, $J_{gem}$=10Hz, 12-C$\underline{H}$), 2.3–2.8(m, COC$\underline{H}_2$, N-C$\underline{H}_2$), 2.16(d, $J_{5,6}$=2Hz, 5-C$\underline{H}$), 1.7, 1.5, 1.42, 1.32, 1.28, 1.02(s, 5×C$\underline{H}_3$),

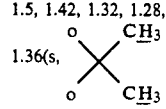

Example 6 (Compound No. 9)
PMR(CDCl$_3$): δ=5.92(d of d, $J_{trans}$=17Hz, $J_{cis}$=10.8Hz, vinylic-$\underline{H}$), 5.28(d, $J_{6,7}$=4Hz, 7-C$\underline{H}$), 5.18(d of d, $J_{trans}$=17Hz, $J_{gem}$=2Hz, vinylic-$\underline{H}$), 4.92(d of d, $J_{cis}$=10.8Hz, $J_{gem}$=2Hz), 4.44(bt, 6C$\underline{H}$), 4.26(bs, 1β-C$\underline{H}$), 3.8–3.6(m, OC$\underline{H}_2$)3.0(d, $J_{gem}$=18Hz, 12-C$\underline{H}$), 2.64 (d, $J_{gem}$=18Hz, 12-C$\underline{H}$), 2.6–2.2(m, NC$\underline{H}_2$), 2.2(d, $J_{5,6}$=3Hz, 5-C$\underline{H}$), 1.7, 1.6, 1.52, 1.44, 1.08, (s, 5×C$\underline{H}_3$),

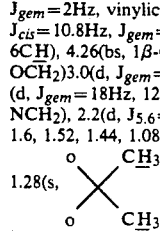

Example 7 (Compound No. 14)
PMR(CDCl$_3$): δ=6.04(d of d, $J_{trans}$=17Hz, $J_{cis}$=10.8Hz, vinylic-$\underline{H}$), 5.84(bt, 6-C$\underline{H}$), 5.10(d of d, $J_{trans}$=17Hz, $J_{gem}$=2Hz, vinylic-$\underline{H}$), 4.92(d of d, $J_{cis}$=10.8Hz, $J_{gem}$=2Hz, vinylic-$\underline{H}$), 4.28(bs, 1β-$\underline{H}$), 4.12(d, $J_{6,7}$=4Hz, 7-C$\underline{H}$), 3.28 (s, OCOC$\underline{H}_2$N), 3.0(d, $J_{gem}$=18Hz, 12-C$\underline{H}$), 2.7(d, $J_{gem}$=18Hz, 12-C$\underline{H}$), 2.6–2.9 (m, C$\underline{H}_2$-N), 2.34(d, $J_{5,6}$=2Hz, 5-C$\underline{H}$), 1.52, 1.44, 1.32, 1.08, 1.0(s, 5×C$\underline{H}_3$),

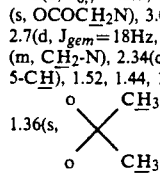

Example 7 (Compound No. 16)
PMR(CDCl$_3$): δ=6.04(d of d, $J_{cis}$=10.8Hz, $J_{trans}$=17Hz, vinylic-$\underline{H}$), 5.81(bt, 6-C$\underline{H}$), 5.12 (d of d, $J_{trans}$=17Hz, $J_{gem}$=2Hz, vinylic-$\underline{H}$), 4.92(d of d, $J_{cis}$=10.8Hz, $J_{gem}$=2Hz, vinylic-$\underline{H}$), 4.28(bs, 1β-C$\underline{H}$), 4.08(d, $J_{6,7}$=4Hz, 7-C$\underline{H}$), 3.0 (d, $J_{gem}$=18Hz, 12-C$\underline{H}$), 2.3–2.8(m, COC$\underline{H}_2$, N-C$\underline{H}_2$), 1.5, 1.44, 1.36, 1.28, 1.08, 1.0(s, 5×C$\underline{H}_3$),

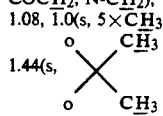

Example 7 (Compound No. 15)
PMR(CDCl$_3$): δ=6.02(d of d, $J_{trans}$=17Hz, $J_{cis}$=10.8Hz, vinylic-$\underline{H}$), 5.84(bt, 6-C$\underline{H}$), 5.12 (d of d, $J_{trans}$=17Hz, $J_{gem}$=2Hz, vinylic-$\underline{H}$), 4.90(d of d, $J_{cis}$=10.8Hz, $J_{gem}$=2Hz, vinylic-$\underline{H}$), 4.28(bs, 1β-C$\underline{H}$), 4.08(d, $J_{6,7}$=4Hz, 7-C$\underline{H}$), 3.0 (d, $J_{gem}$=18Hz, 12-C$\underline{H}$), 2.62(d, $J_{gem}$=18Hz, 12-C$\underline{H}$), 2.7–2.5(m, C$\underline{H}_2$—C$\underline{H}_2$, 2.24(S, N(C$\underline{H}_3$)$_2$), 1.56, 1.5, 1.3, 1.0(s, 5×C$\underline{H}_3$),

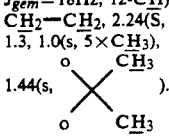

Example 8 (Compound No. 18)
PMR(CDCl$_3$): δ=5.85(d of d, $J_{cis}$=10.8Hz, $J_{trans}$=17Hz, vinylic-$\underline{H}$), 5.75(bt, 6-C$\underline{H}$), 5.3 (d, $J_{6,7}$=4Hz, 7-C$\underline{H}$), 5.1 (d of d, ($J_{trans}$=17 Hz, $J_{gem}$=2Hz, vinylic-$\underline{H}$), 4.86(d of d, $J_{cis}$=10.8Hz, $J_{gem}$=2Hz, vinylic-$\underline{H}$), 4.28(bt, 1β-C$\underline{H}$), 2.3–2.6(m, COC$\underline{H}_2$, N-C$\underline{H}_2$), 2.41(d, $J_{5,6}$=2Hz, 5-C$\underline{H}$), 1.6, 1.52, 1.48, 1.08, 1.04, (s, 5×C$\underline{H}_3$), 2.08(s, OCOC$\underline{H}_3$), Example 8 (Compound No. 17)
PMR(CDCl$_3$): δ=5.9(d of d, $J_{trans}$=17Hz, $J_{cis}$=10.8Hz, vinylic-$\underline{H}$), 5.84(bt, 6-C$\underline{H}$), 5.34 (d, $J_{6,7}$=4Hz, 7-C$\underline{H}$), 5.14(d of d, $J_{trans}$=17Hz, $J_{gem}$=2Hz, vinylic-$\underline{H}$), 4.90(d of d, $J_{cis}$=10.8Hz, $J_{gem}$=2Hz, vinylic-$\underline{H}$), 4.28(bs, 1β-C$\underline{H}$), 3.8(s, OCOC$\underline{H}_2$N), 3.2–3.5(m, N-C$\underline{H}_2$), 3.0(d, $J_{gem}$=18Hz. 12-C$\underline{H}$), 2.66(d, $J_{gem}$=18Hz, 12-C$\underline{H}$), 2.48(d, $J_{5,6}$=2Hz, 5-C$\underline{H}$), 2.04(s, OCOC$\underline{H}_3$), 1.48, 1.44, 1.08, 1.0 (s, 5×C$\underline{H}_3$), Example 8 (Compound No. 19)
PMR(CDCl$_3$): δ=5.92(d of d, $J_{cis}$=10.8Hz, $J_{trans}$=17Hz, vinylic-$\underline{H}$), 5.8(bt, 6-C$\underline{H}$), 5.30 (d, $J_{6,7}$=4Hz, 7-C$\underline{H}$), 5.16(d of d, $J_{trans}$=17Hz, $J_{gem}$=2Hz, vinylic-$\underline{H}$), 4.88(d of d, $J_{cis}$=10.8Hz, $J_{gem}$=2Hz, vinylic-$\underline{H}$), 4.26(bs, 1β-C$\underline{H}$), 3.0 (d, $J_{gem}$18Hz, 12-C$\underline{H}$), 2.62(d, $J_{gem}$=18Hz, 12-C$\underline{H}$), 2.5–2.7(m, C$\underline{H}_2$—C$\underline{H}_2$), 2.4(d, $J_{5,6}$=2Hz, 5-C$\underline{H}$), 2.24(s, N(C$\underline{H}_3$)$_2$), 2.0(s, OCOC$\underline{H}_3$), 1.56, 1.50, 1.44, 1.0(s, 5×CH$_3$),

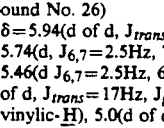

Example 9 (Compound No. 26)
PMR(CDCl$_3$): δ=5.94(d of d, $J_{trans}$=17Hz, $J_{cis}$=10.8Hz, 5.74(d, $J_{6,7}$=2.5Hz, 7-C$\underline{H}$), 5.46(d $J_{6,7}$=2.5Hz, 6C$\underline{H}$), 5.3(d, of d, $J_{trans}$=17Hz, $J_{gem}$=2Hz, vinylic-$\underline{H}$), 5.0(d of d, $J_{cis}$=10.8Hz, $J_{gem}$=2Hz, vinylic-$\underline{H}$), 4.7(bt, 1β-C$\underline{H}$), 3.1(d, $J_{gem}$=18Hz, 12-C$\underline{H}$), 2.8(d, NC$\underline{H}_3$), 2.62(d, $J_{gem}$=18Hz, 12C$\underline{H}$), 1.56, 1.4, 1.28, 1.2(s×C$\underline{H}_3$), 4.7(bs, NH).

Example 9 (Compound No. 24)
PMR(CDCl$_3$): δ=5.92(d of d, $J_{trans}$=17Hz, $J_{cis}$=10.8Hz, vinylic-$\underline{H}$), 5.80(bt, 6-C$\underline{H}$), 5.48(d, $J_{6,7}$=4Hz, 7-C$\underline{H}$), 5.18(d of d, $J_{trans}$=17Hz, $J_{gem}$=2Hz, vinylic-$\underline{H}$), 4.92(d of d, $J_{cis}$=10.8Hz, $J_{gem}$=2Hz, vinylic-$\underline{H}$), 4.56(bs, 1-C$\underline{H}$),

TABLE VII-continued
PMR DATA FOR THE ABOVE WORKING EXAMPLES

Working Examples 3.20(d, $J_{gem}$=18Hz, 12-C$\underline{H}$), 2.8–2.4(m, NC$\underline{H}_3$), 2.0(s, OCOC$\underline{H}_3$), 1.68, 1.48, 1.4, 1.10, 1.04(s, 5×C$\underline{H}_3$), 2.28(s, N(C$\underline{H}_3)_2$), 6.16((bs, 9-O$\underline{H}$).

We claim:

1. A process for the preparation of a 6-acyl-, 7-acyl- or 6,7-diacyl analogue of forskolin of the general formula I

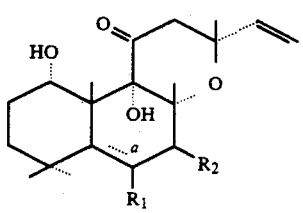
(I)

wherein
each of $R_1$ and $R_2$ is independently hydroxyl, acetoxy, a group

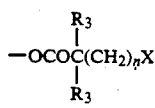

wherein $R_3$ is hydrogen or alkyl,
n is from 0 to 10,
X is hydrogen, halogen, alkyl or a group —NR$_4$R$_5$, wherein $R_4$ and $R_5$ when they are the same are hydrogen or alkyl; when they are not the same $R_4$ is hydrogen and $R_5$ is: (1) alkyl; (2) phenyl, which may optionally be substituted at one or more positions by $C_1$–$C_4$-alkyl, $C_1$–$C_4$-alkoxy, hydroxy, halogen, cyano, nitro, or trifluoromethyl; (3) benzyl, which may optionally be substituted at one or more positions by $C_1$–$C_4$-alkyl, $C_1$–$C_4$-alkoxy, hydroxy, halogen, cyano, nitro, or trifluoromethyl; or $R_4$ and $R_5$ together with the nitrogen to which they are attached form a heterocycle selected from the group consisting of piperidino, morpholino, piperazino, pyrrolidino and homopiperadino, said heterocycle optionally being substituted at one or more positions by halogen, alkyl, hydroxy, alkoxy, carboxyl, nitro, or cyano;
or a group —OCONR$_6$R$_7$, wherein R$_6$ and R$_7$ have the same meaning as defined for R$_4$ and R$_5$, respectively;
wherein "a" is an optional additional bond between the carbon atoms C-5 and C-6, with the proviso that when it is present, $R_1$ is hydrogen only and $R_2$ has the same meaning as defined above, or a pharmaceutically acceptable salt thereof,
which comprises removing the 1,9-O-isopropylidene protective group from compounds of the general formula II

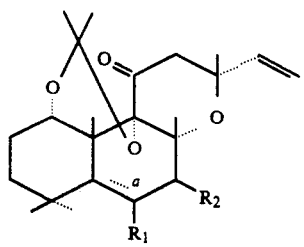
(II)

wherein $R_1$, $R_2$ and "a" have the meanings defined above, by adjusting the pH of the solution to 1.0–3.5 at a temperature ranging from 0° to 60° C. for a period of up to 72 hours, and, if desired, converting the obtained compound into a pharmaceutically acceptable salt thereof.

2. A compound of the formula II (II)

wherein
each of $R_1$ and $R_2$ is independently hydroxyl, acetoxy, a group

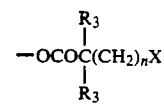

wherein $R_3$ is hydrogen or alkyl,
n is from 0 to 10,
X is hydrogen, halogen, alkyl or a group —NR$_4$R$_5$, wherein $R_4$ and $R_5$ when they are the same are hydrogen or alkyl; when they are not the same $R_4$ is hydrogen and $R_5$ is: (1) alkyl; (2) phenyl, which may optionally be substituted at one or more positions by $C_1$–$C_4$-alkyl, $C_1$–$C_4$-alkoxy, hydroxy, halogen, cyano, nitro, or trifluoromethyl; (3) benzyl, which may optionally be substituted at one or more positions by $C_1$–$C_4$-alkyl, $C_1$–$C_4$-alkoxy, hydroxy, halogen, cyano, nitro, or trifluoromethyl; or $R_4$ and $R_5$ together with the nitrogen to which they are attached form a heterocycle selected from the group consisting of piperidino, morpholino, piperazino, pyrrolidino and homopiperadino, said heterocycle optionally being substituted at one or more positions by halogen, alkyl, hydroxy, alkoxy, carboxyl, nitro, or cyano;
or a group —OCONR$_6$R$_7$, wherein R$_6$ and R$_7$ have the same meaning as defined for R$_4$ and R$_5$, respectively;
wherein "a" is an optional additional bond between the carbon atoms C-5 and C-6, with the proviso that when it is present, $R_1$ is hydrogen only and $R_2$ has the same meaning as defined above.

3. The process of claim 1, wherein the pH value of the solution is adjusted while the solution is at a temperature from 25° C. to 60° C.

4. The process of claim 1, wherein the pH value of the solution is adjusted while the solution is at a temperature from 30° C. to 40° C.

5. The process of claim 1, wherein $R_5$ is phenyl substituted at one or more positions by a halogen selected from the group consisting of chlorine and fluorine.

6. The process of claim 1, wherein $R_5$ is benzyl substituted at one or more positions by a halogen selected from the group consisting of chlorine and fluorine.

7. The compounds of claim 2, wherein $R_5$ is phenyl substituted at one or more positions by a halogen selected from the group consisting of chlorine and fluorine.

8. The compound of claim 2, wherein $R_5$ is benzyl substituted at one or more positions by a halogen selected from the group consisting of chlorine and fluorine.

9. The process of claim 1, wherein the pH value of the solution is adjusted while the solution is at a temperature from 15° C to 20° C.

* * * * *